United States Patent
Enan et al.

(10) Patent No.: US 10,064,836 B2
(45) Date of Patent: Sep. 4, 2018

(54) ANTIPARASITIC COMPOSITIONS AND METHODS

(71) Applicant: TyraTech, Inc., Morrisville, NC (US)

(72) Inventors: Essam Enan, Davis, CA (US); Ahmad Akashe, Mundelein, IL (US); Anilkumar Gaonkar, Buffalo Grove, IL (US); Leslie West, Winnetka, IL (US)

(73) Assignee: TyraTech, Inc., Morrisville, NC (US)

( * ) Notice: Subject to any disclaimer, the term of this patent is extended or adjusted under 35 U.S.C. 154(b) by 0 days.

(21) Appl. No.: 14/418,067

(22) PCT Filed: Aug. 5, 2013

(86) PCT No.: PCT/US2013/053651
§ 371 (c)(1),
(2) Date: Jan. 28, 2015

(87) PCT Pub. No.: WO2014/022859
PCT Pub. Date: Feb. 6, 2014

(65) Prior Publication Data
US 2015/0150838 A1 Jun. 4, 2015

Related U.S. Application Data

(60) Provisional application No. 61/679,523, filed on Aug. 3, 2012.

(51) Int. Cl.
| | | |
|---|---|---|
| *A61K 31/235* | (2006.01) | |
| *A61K 31/015* | (2006.01) | |
| *A61K 31/22* | (2006.01) | |
| *A61K 31/05* | (2006.01) | |
| *A61K 31/21* | (2006.01) | |

(52) U.S. Cl.
CPC .......... *A61K 31/235* (2013.01); *A61K 31/015* (2013.01); *A61K 31/05* (2013.01); *A61K 31/21* (2013.01); *A61K 31/22* (2013.01)

(58) Field of Classification Search
None
See application file for complete search history.

(56) References Cited

U.S. PATENT DOCUMENTS

| | | |
|---|---|---|
| 3,943,063 A | 3/1976 | Morishita et al. |
| 3,971,852 A | 7/1976 | Brenner et al. |
| 4,211,668 A | 7/1980 | Tate |
| 5,407,609 A | 4/1995 | Tice et al. |
| 5,418,010 A | 5/1995 | Janda et al. |
| 7,541,155 B2 | 6/2009 | Enan |
| 7,622,269 B2 | 11/2009 | Enan |
| 8,501,247 B2 | 8/2013 | Enan et al. |
| 8,507,013 B2 | 8/2013 | Enan |
| 8,685,471 B2 | 4/2014 | Enan |
| 8,691,256 B2 | 4/2014 | Enan |
| 8,734,869 B2 | 5/2014 | Enan |
| 8,865,230 B2 | 10/2014 | Enan |
| 9,492,490 B1 | 11/2016 | Enan |
| 2006/0263403 A1 | 11/2006 | Enan |
| 2008/0047312 A1 | 2/2008 | Hill et al. |
| 2008/0075796 A1 | 3/2008 | Enan |
| 2008/0145462 A1 | 6/2008 | Enan |
| 2009/0099135 A1 | 4/2009 | Enan |
| 2009/0232918 A1 | 9/2009 | Enan |
| 2010/0310666 A1 | 12/2010 | Gaonkar et al. |
| 2011/0003317 A1 | 1/2011 | Enan |
| 2011/0008471 A1 | 1/2011 | Enan |
| 2011/0159103 A1* | 6/2011 | Akashe |
| 2011/0171135 A1 | 7/2011 | Enan |
| 2014/0377385 A1 | 12/2014 | Enan |
| 2015/0087516 A1 | 3/2015 | Enan |
| 2015/0201615 A1 | 7/2015 | Schmidt et al. |
| 2016/0029625 A1 | 2/2016 | Kennedy et al. |
| 2016/0165899 A1 | 6/2016 | Bissinger et al. |
| 2017/0094963 A1 | 4/2017 | Enan |

FOREIGN PATENT DOCUMENTS

WO    WO 2010/067199 A2    6/2010

OTHER PUBLICATIONS

Davis, A., "Drug treatment in Intestinal Heiminthiases", World Health Organization, Geneva, 1973, pp. 104-107.
Pearson et al., "Praziquantel: A Major Advance in Anthelminthic Therapy", Annals of Internal Medicine, 1993, vol. 99, pp. 195-198.

* cited by examiner

*Primary Examiner* — Savitha M Rao
*Assistant Examiner* — Gregg Polansky
(74) *Attorney, Agent, or Firm* — K&L Gates LLP

(57) ABSTRACT

Compositions and methods for treating parasitic infections are provided. The compositions can include two or more of alpha-pinene, linalyl acetate, para-cymene, and thymol octanoate. The compositions and methods can be effective against, for example, protozoan parasites, helminthic parasites, nematodes, trematodes, flukes, cestodes, and the like. Formulations made from the composition are also provided, including formulations in which the composition is combined with a carrier to form a food product and/or a drink. The formulation can be, for example, a suspension, a solution, or an emulsion in an oily or an aqueous carrier; likewise, the composition can be provided in an encapsulated or microencapsulated form.

48 Claims, 3 Drawing Sheets

ANTIPARASITIC COMPOSITIONS AND METHODS

CROSS-REFERENCE TO RELATED APPLICATIONS

The present application is a U.S. National Stage entry under 35 U.S.C. § 371 of International Application No. PCT/US2013/053651, filed on Aug. 5, 2013, designating the United States of America and published in English on Feb. 6, 2014, which in turn claims priority to U.S. Provisional Application No. 61/679,523, filed on Aug. 3, 2012, each of which is hereby incorporated by reference in its entirety.

FIELD OF THE INVENTION

The invention disclosed herein generally relates to compositions and methods related to antiparasitics.

BACKGROUND OF THE INVENTION

Parasitic infections of plants, humans, and other animals pose a worldwide problem. For example, more than 650 million people are at risk for gastrointestinal parasitic infection, and about 200 million are actually infected. Various conditions contribute to the development and spread of parasitic infections, including poor sanitary conditions; low host resistance; population expansion; and inadequate control of vectors and infection reservoirs.

Such parasitic infections present an abundance of medical and social problems. For example, parasitic infection can undermine child development, educational achievement, reproductive health, and social and economic development. Indeed, some parasitic infections can cause morbidity and mortality. Notwithstanding the severe impact that parasitic infections can have, relatively few treatment options are available.

Available treatments are limited, and treatments for some parasitic infections are non-existent. In the 1960s, niclosamide (also known as yomesan) was identified for use in treating certain helminthic parasitic infections; however, niclosamide has certain drawbacks. For example, in many cases a single dose of niclosamide does not provide a curative effect, rather, a relapse ensues because the compound has difficulty accessing cysticercoids buried deeply within the mucosal villi. As such, satisfactory results require an extended treatment with niclosamide for approximately 7 days. See Davis, Drug treatment of intestinal helminthiasis, World Health Organization (WHO), Geneva, 1973.

Another drug that has been used to treat helminthic parasitic infections is Praziquantel (2-(cyclohexylcarbonyl)-1,2,3,6,7,11b-hexahydro-4H-pyrazino(2,1-a)isoquinolin-4-one; also known as Biltracide). See Pearson and Gurrant, Praziquantel: a major advance in anthelminthic therapy. Annals of Internal Medicine, 99:195-198, 1983. Praziquantel can be administered in a single dose; however, treatment strategies making use of Praziquantel are at risk because of the possibility of the development of resistance to Praziquantel. Accordingly, there remains a need in the art for non-harmful compositions that are effective for treating parasitic infections.

SUMMARY OF THE INVENTION

Compositions and methods for treating parasitic infections are provided. The compositions can include two or more of alpha-pinene, linalyl acetate, para-cymene, and thymol octanoate. The compositions and methods can be effective against, for example, protozoan parasites, helminthic parasites, nematodes, trematodes, flukes, cestodes, and the like. Formulations made from the composition are also provided, including formulations in which the composition is combined with a carrier to form a food product and/or a drink. The formulation can be, for example, a suspension, a solution, or an emulsion in an oily or an aqueous carrier; likewise, the composition can be provided in an encapsulated or microencapsulated form.

Unless otherwise noted, terms are to be understood according to conventional usage by those of ordinary skill in the relevant art.

The invention disclosed herein relates to compositions and methods related to antiparasitics.

In some embodiments, the parasitic infections are caused by parasites classified as endoparasites, ectoparasites, human parasites, animal parasites, or agricultural parasites.

In some embodiments, the composition for treating a parasitic infection in a subject includes two or more compounds selected from: alpha-pinene, linalyl acetate, para-cymene, and thymol octanoate. In some embodiments, the composition includes three or more compounds selected from: alpha-pinene, linalyl acetate, para-cymene, and thymol octanoate. In some embodiments, the composition includes alpha-pinene, linalyl acetate, para-cymene, and thymol octanoate.

In some embodiments, the composition includes 20-30% by weight alpha-pinene, 20-30% by weight linalyl acetate, 20-30% by weight para-cymene, and 20-30% by weight thymol octanoate. In some embodiments, the composition includes 25% by weight alpha-pinene, 25% by weight linalyl acetate, 25% by weight para-cymene, and 25% by weight thymol octanoate.

In some embodiments, the antiparasitic composition can be comprised of 1-5%, 5-15%, 10-30%, 25-40%, 10-50%, or 40%-75% alpha-pinene. In some embodiments, the antiparasitic composition can be comprised of 1-5%, 5-15%, 10-30%, 25-40%, 10-50%, or 40%-75% linalyl acetate. In some embodiments, the antiparasitic composition can be comprised of 1-5%, 5-15%, 10-30%, 25-40%, 10-50%, or 40%-75% para-cymene. In some embodiments, the antiparasitic composition can be comprised of 1-5%, 5-15%, 10-30%, 25-40%, 10-50%, or 40%-75% thymol octanoate.

In some embodiments, the parasitic infection is by a protozoan parasite. In some embodiments, the parasite is selected from intestinal protozoa, tissue protozoa, and blood protozoa. In some embodiments, the parasite is selected from: *Entamoeba hystolytica, Giardia lamblia, Cryptosporidium muris, Cryptosporidium parvum, Trypanosomatida gambiense, Trypanosomatida rhodesiense, Trypanosomatida crusi, Leishmania mexicana, Leishmania braziliensis, Leishmania tropica, Leishmania donovani, Toxoplasma gondii, Plasmodium vivax, Plasmodium ovale, Plasmodium malariae, Plasmodium falciparum, Trichomonas vaginalis*, and *Histomonas meleagridis*.

In some embodiments, the parasitic infection is by a helminthic parasite. In some embodiments, the parasite is selected from nematodes. In some embodiments, the parasite is selected from Adenophorea. In some embodiments, the parasite is selected from Secernentea. In some embodiments, the parasite is selected from: *Trichuris trichiura, Ascaris lumbricoides, Enterobius vermicularis, Ancylostoma duodenale, Necator americanus, Strongyloides stercoralis, Wuchereria bancrofti, Dracunculus medinensis*. In some embodiments, the parasite is selected from trematodes. In some embodiments, the parasite is selected from: blood flukes, liver flukes, intestinal flukes, and lung flukes. In some embodiments, the parasite is selected from: *Schistosoma mansoni, Schistosoma haematobium, Schistosoma japonicum, Fasciola hepatica, Fasciola gigantica, Heterophyes heterophyes, Paragonimus westermani,* and *Opishorchis sinensis.*

In some embodiments, the parasite is selected from cestodes. In some embodiments, the parasite is selected from *Taenia solium, Taenia saginata, Hymenolepis nana, Echinococcus granulosus,* and *Diplyidium caninum.*

In some embodiments, the composition is provided in a formulation. The formulation can include the composition and a carrier, such as a food product. In some embodiments the formulation includes the composition encapsulated or microencapsulated with an outer shell material.

The presently-disclosed subject matter includes a method of treating a parasitic infection in a subject. In some embodiments, the method includes administering to the subject an effective amount of a composition as described herein.

It is contemplated that the compositions of the presently-disclosed subject matter can be formulated for and delivered by carriers, including food products. For example, additives are added to baked goods, such as cookies, breads, cakes, etc., to enhance or modify flavor or color, increase shelf life, enhance their nutritional value, and generally produce a desired effect. Similarly, compositions of the presently-disclosed subject matter can be formulated with food products as carriers and delivered by ingestion to produce their desired effect. Of course, numerous types of foods can be used to deliver the compositions, including but not limited to: beverages, breakfast cereals, and powdered drink mixes.

Further, the compositions disclosed herein can take such forms as suspensions, solutions or emulsions in oily or aqueous carriers, and can contain formulatory agents such as suspending, stabilizing and/or dispersing agents. For oral administration, the compositions can take the form of, for example, tablets or capsules prepared by a conventional technique with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods known in the art. For example, a composition disclosed herein can be formulated having an enteric or delayed release coating which protects the composition until it reaches the colon.

Liquid preparations for oral administration can take the form of, for example, solutions, syrups or suspensions. Such liquid preparations can be prepared by conventional techniques with pharmaceutically acceptable additives such as suspending agents (e.g., sorbitol syrup, cellulose derivatives or hydrogenated edible fats); emulsifying agents (e.g., lecithin or *acacia*); non-aqueous vehicles (e.g., almond oil, oily esters, ethyl alcohol or fractionated vegetable oils); and preservatives (e.g., methyl or propyl-p-hydroxybenzoates or sorbic acid). Liquid preparations for oral administration can also be formulated for delayed release, such as for example in "gel caps."

In some embodiments, the compositions can be provided in an encapsulated or microencapsulated form. Microencapsulation is a process where small particles of the composition are coated or encapsulated with an outer shell material for controlling the release of the composition or for protecting the composition. Exemplary outer shell material includes proteins, polysaccharides, starches, waxes, fats, natural and synthetic polymers, and resins. Microencapsulation can be done either chemically or physically. For example, physical methods of encapsulating the compositions can include: spray drying, spray chilling, pan coating, or coextrusion. Chemical methods of encapsulation can include coacervation, phase separation, solvent extraction, or solvent evaporation.

As one example, for coextrusion of a liquid core, liquid core and shell materials are pumped through concentric orifices, with the core material flowing in the central orifice, and the shell material flowing through the outer annulus. An enclosed compound drop is formed when a droplet of core fluid is encased by a layer of shell fluid. The shell is then hardened by appropriate means; for example, by chemical cross-linking in the case of polymers, cooling in the case of fats or waxes, or solvent evaporation. Additional information about methods and systems for providing compositions formulated for and delivered via food products can be found in U.S. Pat. Nos. 5,418,010, 5,407,609, 4,211,668, 3,971,852, and 3,943,063, each of which is incorporated herein by this reference.

DETAILED DESCRIPTION OF THE INVENTION

Figure 1:
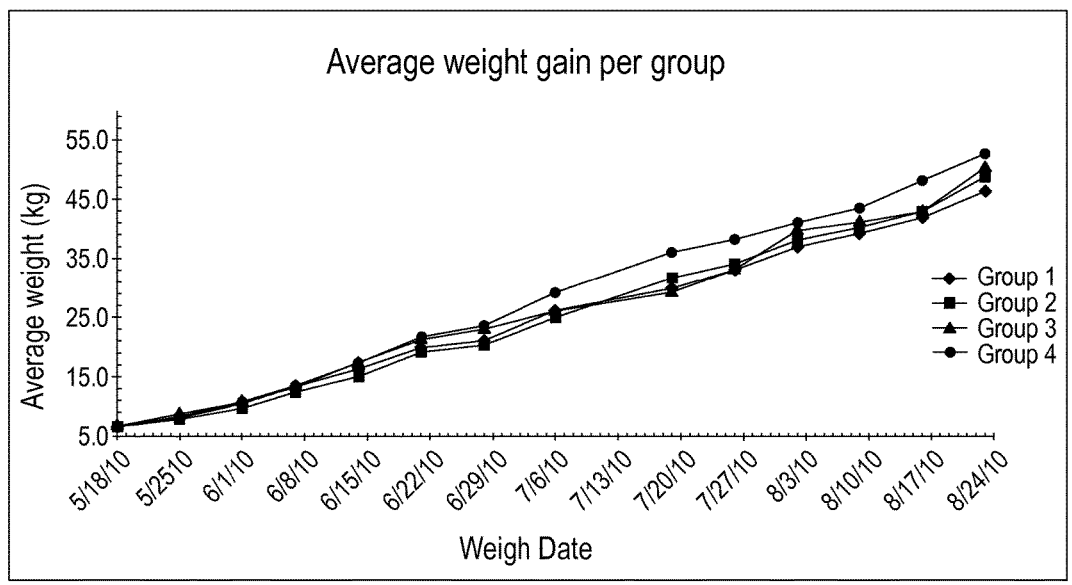
FIG. 1 is series of line graphs representing weekly body weights of four groups of animals infected with *Ascaris suum* and treated with compounds disclosed herein.

As used herein, the terms "host" and "subject" are used interchangeably and refer to a plant or an animal capable of being infected by a parasite. The animal can be a vertebrate. The vertebrate can be warm-blooded. The warm-blooded vertebrate can be a mammal. The mammal can be a human. The human can be an adult or a child. As used herein, the terms "host" and "subject" include human and animal hosts and subjects. Thus, veterinary therapeutic uses are provided in accordance with the presently-disclosed subject matter. As such, the presently-disclosed subject matter provides for the treatment of mammals such as humans, as well as those mammals of importance due to being endangered, such as Siberian tigers or snow leopards; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

As used herein, the terms "treat," "treating," and "treatment" refer to: conferring protection against infection; preventing infection; alleviating infection; reducing the severity of symptoms and/or sequelae of infection; eliminating infection; and/or preventing relapse of infection. As used herein, the terms "treat," "treating," and "treatment" also refer to conferring protection against, preventing, alleviating, reducing the severity of, eliminating, and/or preventing relapse associated with a disease or symptoms caused by a parasitic infection.

As used herein, the term "effective amount" refers to a dosage sufficient to provide treatment for a parasitic infection. The exact amount that is required can vary, for example, depending on the target parasite, the treatment being affected, age and general condition of the subject, the particular formulation being used, the mode of administration, and the like. As such, the effective amount will vary based on the particular circumstances, and an appropriate effective amount can be determined in a particular case by one of ordinary skill in the art using only routine experimentation.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Antiparasitic Efficacy of a Novel Functional Food Compound Using *Ascaris Suum* Model in Pigs A controlled efficacy study was performed in pigs infected with *Ascaris suum* to determine the efficacy of daily administration of one of three essential oil-comprising experimental blends on worm establishment and egg output.

64 female Yorkshire-cross pigs were received at the University of Georgia Veterinary Bioresources Facility (VBF). All pigs were 21-24 days of age at the time of arrival. After arrival, pigs were acclimated for 3 days, before starting the study. Four groups of 16 pigs were included in the study. All pigs were weighed upon arrival at the VBF, stratified by weight, blocked into groups of 4, and then within block they were assigned randomly to treatment group.

One group served as an untreated control that received control article at a dosage of 1.0 mg/kg (group 4) and the other 3 groups received experimental blends. One group received a previously manufactured lot of experimental blend at 1.0 mg/kg (group 1), and 2 groups received a newly manufactured lot of experimental blend at a dose of either 0.5 (group 3), or 1.0 mg/kg (group 2). Beginning on the $3^{rd}$ day after arrival at the VBF, experimental blend or control article was administered inside an Oreo cookie daily (7 days each week) to each pig for the duration of the study (15 weeks). After receiving daily treatment with experimental blend for 3 days, inoculation with *Ascaris suum* eggs was started at a dose of 20 eggs/kg/week for 4 weeks, administered daily, Monday through Friday. Blood was drawn at the start of the study from most of the pigs and at necropsy from all pigs. Once each week, pigs were weighed and starting at week 6 feces were collected weekly for fecal egg counts (FEC). The amount of experimental blend and the number of eggs administered to the pigs was adjusted each week based on their weights. Approximately 10 weeks after the final inoculation with *A. suum* eggs, pigs were necropsied over a period of 4 days. At necropsy the entire contents of the small intestine were retrieved and worms were separated from intestinal contents. All worms were counted, measured, and identified to sex. Also at necropsy blood, urine and fecal samples were taken. A sample of feces was used for a fecal egg count and a second sample was collected for microbiological analysis. Based on the observed reduction in worm counts, there appeared to be a dose dependent effect of the Group 2 and Group 3 experimental blends on the number of parasites infecting the pigs. The Group 1 experimental blend appeared to have little effect on the worm burdens of the pigs. The Group 2 and Group 3 experimental blends at doses of 0.5 and 1.0 mg/kg yielded a reduction in worm counts of 39.3% and 76.8%, respectively. There was also a significant reduction in numbers of female worms for the Group 2 experimental blend 1.0 mg/kg dose compared to the control group (Group 4). Numbers of male worms, worm volume and FEC were analyzed across all groups; in all cases the p-value approaches the arbitrary significance cutoff of 0.05, ranging from 0.06 to 0.14 among the various parameters tested. The inability to detect significance in these parameters when examining data from all groups was likely due to a reduction in power caused by the very high levels of variability in the data of Groups 1 and 3. Therefore, the analysis was repeated omitting the data from groups 1 and 3. The direct comparisons made between the control group (group 4) and the Group 2 experimental blend 1.0 mg/kg dose, revealed a significant difference between the groups for all of these parameters. With regard to pig weights, there were significant differences across time for all treatment groups. All pigs in all groups (with the exception of a single pig that died during the study) remained clinically normal and showed no signs of reduced intestinal health.

The administration of each of the three essential oil-comprising experimental blends was well tolerated by all pigs and did not cause any apparent adverse effects on the health. The Group 2 experimental blend administered at a dose of 1.0 mg/kg yielded a statistically and a biologically significant reduction in worm counts compared to untreated controls.

Study Schedule

| Week | Treatment |
|---|---|
| 1 | Receive pigs, Weigh, dose daily starting day 4 |
| 2 | Weigh, Bleed, Vaccinate, FEC, Infect 20 ova/kg, dose daily |
| 3 | Weigh, Infect 20 ova/kg, dose daily |
| 4 | Weigh, Infect 20 ova/kg, dose daily |
| 5 | Weigh, Infect 20 ova/kg, dose daily |
| 6 | Weigh, FEC, dose daily |
| 7 | Weigh, FEC, dose daily |
| 8 | Weigh, FEC, dose daily, egg development assay (EDA) |
| 9 | Weigh, FEC, dose daily, EDA |
| 10 | Weigh, FEC, dose daily, EDA |
| 11 | Weigh, FEC, dose daily, EDA |
| 12 | Weigh, FEC, dose daily, EDA |
| 13 | Weigh, FEC, dose daily, EDA |
| 14 | Weigh, FEC, dose daily, EDA |
| 15 | Weigh, FEC, Bleed, Collect Urine, Necropsy pigs and recover worms, EDA |
| 16 | Count and measure worms, EDA, begin microbiological analysis |
| 17 | Count and measure worms, EDA, microbiological analysis |
| 18 | Count and measure worms, EDA, microbiological analysis |
| 19 | Complete compilation of parasitological data, microbiological analysis |
| 20-22 | Submit preliminary report to the sponsor, Submit parasitological data for statistical analysis |
| 23-26 | Complete statistical analysis |
| 27-30 | Prepare and submit final report to TyraTech |

The study was a controlled efficacy trial using a randomized block design. Pigs were ranked by decreasing weight and blocked into groups of four. Each consecutive set of four pigs comprised a replicate. Within each replicate, pigs were allocated randomly to one of four treatment Groups, each comprised of 16 animals. See Table 1 for details regarding each treatment Group. Treatments were administered orally to pigs once per day throughout the entire study. All pigs were inoculated orally with infective eggs of *A. suum* starting in week two and continuing for 4 weeks. Average total *A. suum* inoculum per pig was 963 eggs. Essential oil-comprising experimental blend treatments and *A. suum* eggs both were delivered to pigs inside of a cream-filled sandwich cookie. Pigs were necropsied in week 18 of the study and worms were recovered, counted and measured.

Essential oil-comprising experimental blend and control article were stored in tightly sealed glass containers in the refrigerator. The amount of test or control article delivered to the pigs each week for a given group was determined each week based on body weight. Each week, all pigs within a group were weighed and then stratified by weight. Any pig that was 20% or heavier than the lightest pig, would constitute the start of a separate subgroup for dosing purposes. All pigs within a subgroup were treated with the same amount of article, within the allowable range. The target dose level for a subgroup was calculated by taking the weight of the heaviest animal in the subgroup in kg times the dose in mg/kg. This amount was set as a minimum, and 20% over this amount was then set as the highest allowable amount. Most pig groups consisted of 2 subgroups throughout the entire study, but occasionally there were one or a few pigs that were "heavy" outliers, and composed a third subgroup. Using this approach, all pigs received as a minimum, the target dose for their respective treatment groups, but some pigs received a greater amount. Once prepared, the gelatin capsules containing the article (within a 20% tolerance) were administered randomly to pigs in that subgroup through a given week. Then the next week, calculations and amount of article delivered to the pigs were adjusted based on the new weights. Just before administering, the gelatin capsule containing the article was placed inside an Oreo cookie, sealed with additional cream filling and placed into a labeled bag with the pig ID number. Bags containing the Oreos with capsules were carried to the animal rooms and administered each day to the pigs. Pigs were observed to be sure that the entire dose was ingested.

TABLE 1

Treatment groups

| Group ID | Treatment | Experimental Blend Compound | Dosage | Route | Animals/Replicate | No. Replicates | Total No. Animals |
|---|---|---|---|---|---|---|---|
| 1 | Yes | alpha-pinene, linalyl acetate, para-cymene, and thymol acetate | 1.0 mg/kg | oral | 1 | 16* | 16* |
| 2 | Yes | alpha-pinene, linalyl acetate, para-cymene, and thymol octanoate | 1.0 mg/kg | oral | 1 | 16 | 16 |
| 3 | Yes | alpha-pinene, linalyl acetate, para-cymene, and thymol octanoate | 0.5 mg/kg | oral | 1 | 16 | 16 |
| 4 | Control | Empty capsules containing no drug | None (1.0 mg/kg equiv) | oral | 1 | 16 | 16 |

*one animal died of a non-treatment related cause during the study, thus only 15 pigs remained in group 1 at the time of necropsy Infective eggs of *A. suum* were acquired from Dr. Joe Urban (Supervisory Microbiologist; USDA Diet, Genomics and Immunology Lab, Beltsville, Md.). These eggs had been used in previous studies, thus infectivity was proven. Eggs were obtained from adult female *A. suum* worms collected at necropsy using published methods (Costello, 1961). Briefly, the distal portion of uteri of mature female worms were dissected free and then mechanically disrupted using a tissue homogenizer. The eggs were separated from the uterine tissue by pouring off the liquid phase containing the eggs. Eggs were then centrifuged 3 times in 0.5N NaOH to remove any residual uterine tissue and to decorticate (remove the external coat) the *Ascaris* eggs. Eggs were rinsed with distilled water and then kept in a tissue culture flask a room temperature for several weeks to allow the eggs to develop to the infective stage. Eggs were then transferred to the refrigerator where they were stored. *Ascaris* eggs are extremely stable and can survive in the refrigerator for years. Upon receipt at UGA, infective eggs were stored in the refrigerator at 4° C. in water. Beginning in week 2 on 24 May 2010, inoculations were started at a dose rate of 20 eggs/kg body weight (based on mean weight of all pigs) per week divided into 5 inoculations given Monday through Friday. Each week the inoculum dose was recalculated based on the new weights. The final inoculation was administered on 18 Jun. 2010. Estimated total number of eggs administered per pig was 963.

TABLE 2

*Ascaris suum* innoculation

|  | dose 1<br>23 eggs/pig | dose 2<br>34 eggs/pig | dose 3<br>38 eggs/pig | dose 4<br>53 eggs/pig | dose 5<br>66 eggs/pig |
|---|---|---|---|---|---|
| Days received | 2 | 5 | 4 | 5 | 5 |
| Dates | May 24, 2010-May 25, 2010 | May 26, 2010-May 28, 2010 & May 31, 2010-Jun. 1, 2010 | Jun. 2, 2010-Jun. 4, 2010 & Jun. 7, 2010 | Jun. 8, 2010-Jun. 11, 2010 & Jun. 14, 2010 | Jun. 15, 2010-Jun. 19, 2010 |
| Total eggs/pig at dose | 46 | 170 | 152 | 265 | 330 |

*Pigs were inoculated at a rate of 4 eggs/kg body weight per day. Estimated total number of *Ascaris suum* eggs/pig over 21 days of inoculation = 963 eggs Test products include a novel food additive and a placebo.

Group 1 received an essential oil-comprising experimental blend ("old Armor"). The active ingredients comprise a proprietary essential oil blend comprising alpha-pinene, linalyl acetate, para-cymene, and thymol acetate. The dosage form was micro-encapsulated powder in enteric-coated capsules. The dosage to be tested was a daily dose of 1.9 mg/kg. The weight of article needed to deliver 1.0 mg/kg dose of active article was 5.6 mg. The product identification was RM042910-3. It was stored in tightly closed glass bottles at 4° C.

Groups 2 and 3 received an essential oil-comprising experimental blend ("new Armor"). The active ingredients comprise a proprietary essential oil blend comprising alpha-pinene, linalyl acetate, para-cymene, and thymol octanoate. The dosage form was microencapsulated powder in enteric-coated capsules. The dosage to be tested was a daily dose of 1.0 mg/kg and 0.5 for Group 2 and Group 3, respectively. The weight of article needed to deliver 1.0 mg/kg dose of active article was 6.5 mg. The product identification was AC050310-1. The lot numbers of base material were RM042010-2 and RM042210-1. It was stored in tightly closed glass bottles at 4° C.

Group 4, the placebo, was a control article. There was no active ingredient. The dosage form was micro-encapsulated. The dosage to be tested was a daily dose of 1.0 mg/kg. The weight of article needed to deliver 1.0 mg/kg dose of active article was 5.3 mg. The product identification was AC042910-1. The lot numbers of base material were RM042710-1 and RM042710-3. It was stored in tightly closed glass bottles at 4° C.

Animals were obtained from Valley Brook Farm in Madison, Ga. Valley Brook Farm is a USDA approved (USDA license #57-B-0131) and satellite site AAALAC accredited housing facility for providing research pigs. They contract qualified personnel that are AALAS certified in animal husbandry, as well as, Good Laboratory Practices. The animals were weighed, examined and assigned to 1 of 4 groups upon arrival. The pigs were in overall good health.

Pigs were acclimated to the test facilities for 3 days prior to beginning the treatment regimen, during which time confinement and management conditions (i.e., husbandry, diet, and water) were identical to those experienced during the remainder of the trial. During the acclimation period the pigs were handled daily by study personnel and fed Oreo cookies so that they would learn to readily accept them by the time the treatment phase was to start.

One pig was found dead in its run. The pig had appeared normal the previous day at the time of treatment. A full necropsy was performed by a board certified veterinary pathologist at the UGA College of Veterinary Medicine. Cause of death was a small intestinal torsion, which likely caused hemorrhagic shock and anemia due to sequestration of blood in the intestinal lumen. Intestinal torsion is not uncommon in pigs, thus this was likely a random event unassociated with the treatment being received by the pig.

Pigs were housed at the Veterinary Bioresource Facility (VBF) at the UGA College of Veterinary Medicine. This is a relatively new facility and is AAALAC accredited. The VBF has approximately 18,000 sq ft of animal care & use space and 3,000 sq ft support space. Pigs were housed in four animal holding rooms, each approximately 640 sq ft. The animal runs in each room measure 8 ft×4 ft=32 sq ft, and there are 12 runs in each room, which are divided so that 6 runs are contiguous on each side of the room. Pigs were divided such that one treatment group was in a single room. There are 6 runs per side (approximately 192 sq ft.), which provided sufficient room for a given group of pigs in this study.

Water was available to pigs ad libitum via automated waters. Pigs were fed a commercial 18% protein lab ration for pigs (Lab Diet, Swine Formula). Amount fed each day was calculated by animal care personnel based on group body weight to meet maintenance and growth demands.

Doses of essential oil-comprising experimental blends and placebo were prepared based on the week(x) day $0_x$ weight for administration on week(x) day $1_x$ through week (x+1) day $0_{x+1}$. Doses were calculated for each treatment subgroup, and the resultant daily dose individually weighed out on a Sartorius precision balance, and then loaded into a #2 gelatin capsule. The capsules for each subgroup were then placed in an amber pill bottle labeled with the animals ID which composed the subgroup. This process was repeated for all animals under test, whether the animal was receiving an essential oil-comprising experimental blend or placebo. The preparation of the doses was accomplished in a separate laboratory to maintain blinding. Once all doses were prepared, they were returned to the main lab for preparation for administration.

The current day's capsule for a given animal is removed from the appropriate pill bottle (of the subgroup), placed inside an Oreo cookie and glued in place using extra Oreo cream filling. The "loaded" cookie is then placed in a ziplock bag, labeled with that animal's ID, and then sealed. Utilizing unused animal runs as isolation runs, each animal is isolated, then given their dose contained in the cookie. The animal is then observed to insure that treatment was consumed and not dropped or spit out.

Upon arrival at the UGA VBF facility (day 1 of week 0), pigs were observed to assess general health and to look for any clinical abnormalities. Full physical examinations were not performed, as this is extremely difficult to carry out on pigs, especially pigs that are nervous and excited due to shipping and the new surroundings. On day 1 of week 0, all pigs were again clinically observed by the PI and the Project Manager who are a licensed veterinarian and licensed veterinary technician, respectively. All pigs were subsequently observed each day throughout the study by at least one of the study personnel.

All pigs were weighed upon arrival and again once each week for the duration of the study. Weekly averages are presented in FIG. 1.

Feces were collected for the performance of fecal egg counts (FEC) once each week, starting on week 6 and again at necropsy. Fecal Egg counts were performed using a modified McMaster method with detection sensitivity of 50 eggs per gram of feces. All FEC data are documented in the study notebook, and are presented in Table 3 and FIGS. 2 and 3.

Blood samples were taken from most animals during week 2 of the study. Samples could not be acquired from a few pigs. Blood samples were collected again from all pigs at the time of necropsy. Blood samples were delivered to the Diagnostic Laboratory at the UGA College of Veterinary Medicine for analysis. Complete Blood Counts (CBC) and serum biochemical profiles were performed on all samples and all values measured were within normal limits. In addition, a serum sample (2 ml) was placed in a cryo-centrifuge tube and was archived in a −20° C. freezer for later analysis if deemed necessary.

Urine samples were collected directly from the bladder at the time of necropsy. Urinalysis was performed using a urine dipstick and the urine sediment was examined visually using microscopy following centrifugation. All urinalysis parameters were within normal limits.

Pigs were euthanized in a manner consistent with guidelines published in the AVMA Guidelines on Euthanasia 2007 Report. Pigs were first heavily sedated using a combination of ketamine, xylazine and acepromazine or Telazol, ketamine and xylazine administered IM. After pigs were in a deep state of anesthesia, they were then euthanized using an overdose of sodium pentobarbital administered by intravenous injection. Euthanasia was performed 1 pig at a time at the VBF in the animal treatment rooms.

Immediately after animals were euthanized, they were brought to the necropsy facility. At necropsy, pigs were placed in left lateral recumbency, and the abdominal cavity was opened. The junction of the pylorus and the proximal duodenum was located and a ligature was placed. Likewise, the junction of the distal ileum and cecum were located and a ligature was placed so that the full length of the small intestine (SI) could be excised. The mesentery was stripped from the SI and the contents of the SI were emptied into a tray by running the SI through closed fingers. The SI was then opened along its entire length using a scissors and the mucosa was scraped by pulling through closed fingers. The intestines were then placed in a bucket and rinsed with saline. After being rinsed the intestines were pulled through a tightly clinched fist to remove saline and any adherent worms or intestinal contents. All contents and rinsings were then poured through and washed over #8 and #18 sieves (2.36 mm and 1.0 mm apertures, respectively). All worms recovered from the sieve were placed in individually labeled plastic containers in saline. In addition, the stomach was excised, opened and inspected visually for worms, however no worms were found in the stomach of any animal.

All worms recovered were counted and then the volume of worms was determined based on water displacement in a large graduated cylinder. Worms were then placed back into containers and 5% formalin was added to preserve the worms. Later, worms were identified to sex and the length of each worm was measured. In some pigs, some worms were placed into 100% ethanol for archiving of worm DNA. All containers with worms were labeled with host ID, date, worm count and investigator's initials.

Two female worms from each pig (if available) were selected randomly and weighed. The uterus from each worm was then dissected free and weighed.

*Clostridium* was enumerated on McClung Toabe Egg Yolk agar after serial dilution; colony phenotypes were confirmed using gram stain. *Clostridium perfringens* ATCC 13124 was used as the media phenotype control. Lecithinase producing *Clostridium* make colonies with white zones. Lipase producing *Clostridium* make colonies with greasy zones. The number of *Clostridium* of each phenotype (lecithinase+, lipase+) and total *Clostridium* were estimated from colony counts. The counts were transformed to Log (base 10) for statistical analysis.

*Bacteroides* was enumerated on *Bacteroides* Bile Esculin (BBE) agar after serial dilution; colony phenotypes were confirmed using gram stain. *Bacteroides fragilis* ATCC 23745 was used as the media phenotype control. *Bacteroides* produce black or grey colonies with black zones. The number of *Bacteroides* was estimated from colony counts. The counts were transformed to Log (base 10) for statistical analysis.

Details of the amount of an essential oil-comprising experimental blend or control article administered to individual pigs were recorded on data sheets which are included in the study notebook. Unused test product was stored in the laboratory refrigerator in sealed glass bottles, and then returned to test laboratory.

Percent reductions in worm counts and in egg counts were calculated using the following formula: [Mean (Control)−Mean (Treated)]/Mean (Control)×100. No statistical measures or analyses were performed on these basic calculations. However, statistical analyses were performed on the raw data counts.

Models for statistical analysis of worm and egg count data included a parameter for weight since one would usually expect parasite burdens to impact animal growth. However, the change in weight was not significantly associated with the mean number of worms or the FEC. Nevertheless, this parameter was included in the analysis, because it was felt that the parameter might be significant in other similar studies, and including it here would allow for consistency in the analysis among studies. Additionally, this parameter was removed from the model and the analysis is repeated. In all cases, the results were the same. Details of the analysis are found in the full statistical report.

Body weights over the course of the study for the 4 groups are shown in FIG. 1. There seem to be significant differences across time for all treatment groups. In some instances the actual weigh date is one day different from the label on the axis. Data from Jul. 13, 2010 are omitted due to a one-time malfunction of the scale used to record weight.

All blood work on all pigs yielded values that are within normal limits. Urinalysis performed on all pigs yielded values that are within normal limits.

All animals appeared healthy throughout the study except for one pig referred to previously, which died to a non-treatment related event. Each of the three essential oil-comprising experimental blends appeared to be very tolerated by the pigs and no adverse reactions or consequences of the treatments are noted.

Figure 2:
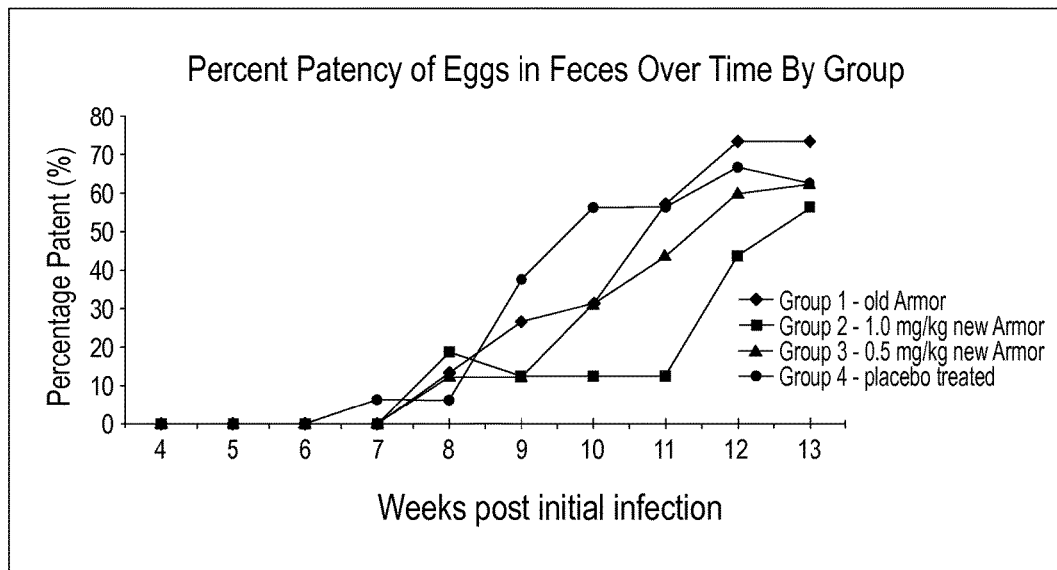
FIG. 2 is a series of line graphs representing the percentage of four groups of animals infected with *Ascaris suum* that had *Ascaris suum* eggs in their feces after treatment of compounds disclosed herein.
Figure 3:
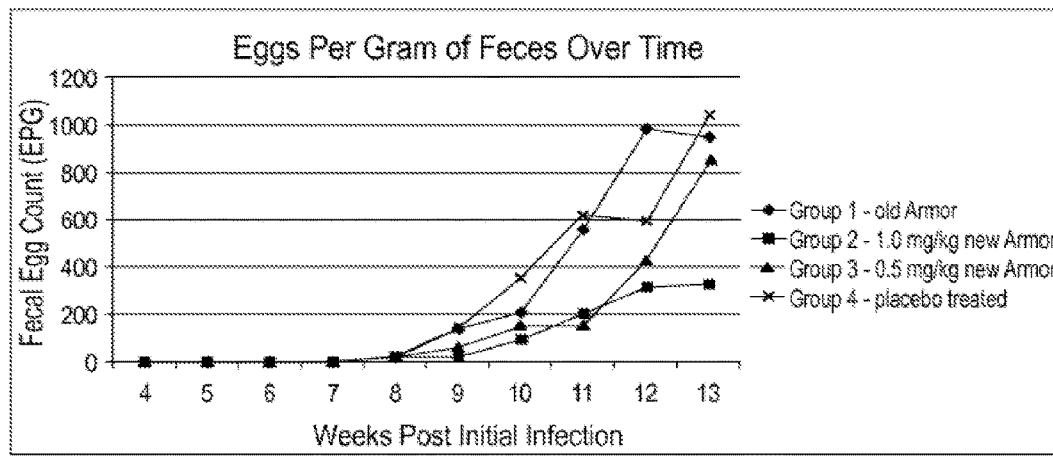
FIG. 3 is a series of line graphs representing the mean *Ascaris suum* eggs per gram of feces of four groups of animals infected with *Ascaris suum* and treated with compounds disclosed herein.
Figure 4:
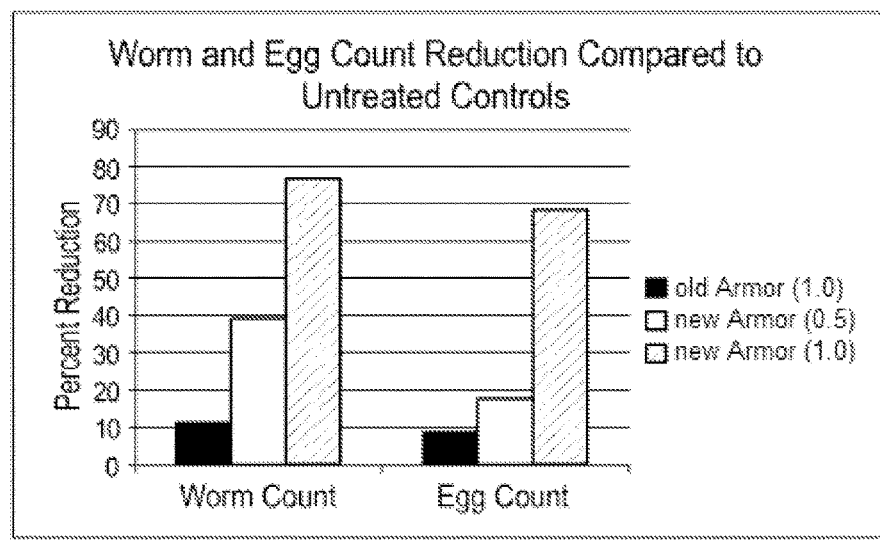
FIG. 4 is a bar graph representing *Ascaris suum* worm and egg count reductions of four groups of animals infected with *Ascaris suum* and treated with compounds disclosed herein compared to control group.

FEC data are shown in Table 3 and FIGS. 2 and 3. FIG. 2 shows the percent of pigs in each group that were passing eggs each week and FIG. 3 shows the mean FEC (in eggs per gram of feces) each week. Table 5 and FIG. 4 show the percent reduction in FEC as compared to the control group.

TABLE 3

Fecal egg counts

| Group | Pig ID | 6/21 | 6/28 | 7/6 | 7/12 | 7/19 | 7/26 | 8/2 | 8/9 | 8/16 | Aug. 23, 2010 (necropsy) |
|---|---|---|---|---|---|---|---|---|---|---|---|
| 1 | 4031 | 0 | 0 | 0 | 0 | 0 | 0 | 50 | 300 | 1450 | 2150 |
| 1 | 4037 | 0 | 0 | 0 | 0 | 0 | 0 | 0 | 0 | 200 | 350 |
| 1 | 4040 | 0 | 0 | deceased | | | | | | | |
| 1 | 4042 | 0 | 0 | 0 | 0 | 0 | 0 | 0 | 0 | 0 | 0 |
| 1 | 4047 | 0 | 0 | 0 | 0 | 50 | 650 | 650 | 2100 | 2750 | 4300 |
| 1 | 4053 | 0 | 0 | 0 | 0 | 250 | 900 | 1300 | 1000 | 550 | 800 |
| 1 | 4060 | 0 | 0 | 0 | 0 | 0 | 0 | 0 | 1050 | 2500 | 250 |
| 1 | 4062 | 0 | 0 | 0 | 0 | 0 | 200 | 550 | 1100 | 900 | 2000 |
| 1 | 4077 | 0 | 0 | 0 | 0 | 0 | 0 | 0 | NA | 1850 | 950 |
| 1 | 4086 | 0 | 0 | 0 | 0 | 0 | 0 | 0 | 0 | 0 | 0 |
| 1 | 4092 | 0 | 0 | 0 | 0 | 0 | 0 | 0 | 0 | 0 | 50 |
| 1 | 4094 | 0 | 0 | 0 | 0 | 0 | 0 | 0 | 200 | 1550 | 1800 |
| 1 | 4100 | 0 | 0 | 0 | 0 | 0 | 350 | 600 | 1900 | 2350 | 950 |
| 1 | 4145 | 0 | 0 | 0 | 0 | 0 | 0 | 0 | 0 | 0 | 0 |
| 1 | 4146 | 0 | 0 | 0 | 0 | 0 | 0 | 0 | 0 | 400 | 650 |
| 1 | 4150 | 0 | 0 | 0 | 0 | 0 | 0 | 0 | 150 | 250 | 0 |
| Mean EPG | | 0.0 | 0.0 | 0.0 | 0.0 | 20.0 | 140.0 | 210.0 | 557.1 | 983.3 | 950.0 |
| 2 | 4035 | 0 | 0 | 0 | 0 | 0 | 0 | 0 | 0 | 0 | 0 |
| 2 | 4043 | 0 | 0 | 0 | 0 | 0 | 0 | 0 | 0 | 50 | 100 |
| 2 | 4048 | 0 | NA | 0 | 0 | 0 | 0 | 0 | 0 | 0 | 0 |
| 2 | 4049 | 0 | 0 | 0 | 0 | 0 | 0 | 0 | 0 | 0 | 0 |
| 2 | 4061 | 0 | 0 | 0 | 0 | 0 | 0 | 0 | 0 | 0 | 0 |
| 2 | 4078 | 0 | 0 | 0 | 0 | 0 | 0 | 0 | 0 | 150 | 1050 |
| 2 | 4080 | 0 | 0 | 0 | 0 | 0 | 0 | 0 | 0 | 50 | 400 |
| 2 | 4083 | 0 | 0 | 0 | 0 | 0 | 0 | 0 | 0 | 150 | 200 |
| 2 | 4085 | 0 | 0 | 0 | 0 | 150 | 150 | 950 | 1700 | 2350 | 1600 |
| 2 | 4091 | 0 | 0 | 0 | 0 | 0 | 0 | 0 | 0 | 0 | 150 |
| 2 | 4093 | 0 | 0 | 0 | 0 | 0 | 0 | 0 | 0 | 100 | 350 |
| 2 | 4097 | 0 | 0 | 0 | 0 | 50 | 0 | 0 | 0 | 0 | 50 |
| 2 | 4099 | 0 | NA | 0 | 0 | 150 | 250 | 550 | 1600 | 2200 | 1350 |
| 2 | 4143 | 0 | 0 | 0 | 0 | 0 | 0 | 0 | 0 | 0 | 0 |
| 2 | 4148 | 0 | 0 | 0 | 0 | 0 | 0 | 0 | 0 | 0 | 0 |
| 2 | 4152 | 0 | 0 | 0 | 0 | 0 | 0 | 0 | 0 | 0 | 0 |
| Mean EPS | | 0.0 | 0.0 | 0.0 | 0.0 | 21.9 | 25.0 | 93.8 | 206.3 | 315.6 | 328.1 |
| 3 | 4026 | 0 | 0 | 0 | NA | 0 | 0 | 0 | 0 | 50 | 0 |
| 3 | 4027 | 0 | 0 | 0 | 0 | 0 | 0 | 50 | 200 | 800 | 950 |
| 3 | 4028 | 0 | 0 | NA | 0 | 0 | 0 | 0 | 0 | 0 | 0 |
| 3 | 4030 | 0 | 0 | 0 | 0 | 0 | 0 | 0 | 0 | 0 | 0 |
| 3 | 4034 | 0 | 0 | 0 | 0 | 200 | 300 | 950 | 1300 | 1900 | 4550 |
| 3 | 4038 | 0 | 0 | 0 | 0 | 0 | 0 | 350 | 200 | 600 | 1150 |
| 3 | 4044 | 0 | 0 | 0 | 0 | 0 | 0 | 0 | 0 | 0 | 200 |
| 3 | 4046 | 0 | NA | NA | 0 | 0 | 0 | 0 | 350 | 400 | 2000 |
| 3 | 4056 | 0 | 0 | 0 | 0 | 0 | NA | 0 | 0 | 0 | 0 |
| 3 | 4076 | 0 | 0 | 0 | 0 | 0 | 0 | 0 | 0 | 0 | 50 |
| 3 | 4084 | 0 | 0 | 0 | 0 | 0 | 0 | 0 | 0 | 0 | 0 |
| 3 | 4088 | 0 | 0 | 0 | 0 | 0 | 0 | 0 | 0 | NA | 0 |
| 3 | 4095 | 0 | 0 | 0 | 0 | 0 | 0 | 200 | 250 | 500 | 950 |
| 3 | 4096 | 0 | 0 | 0 | 0 | 0 | 0 | 0 | 150 | 800 | 400 |
| 3 | 4144 | 0 | 0 | 0 | 0 | 0 | 0 | 0 | 0 | 350 | 950 |
| 3 | 4149 | 0 | 0 | 0 | 0 | 150 | 650 | 950 | 100 | 1050 | 2500 |
| Mean EPG | | 0.0 | 0.0 | 0.0 | 0.0 | 21.9 | 63.3 | 156.3 | 159.4 | 430.0 | 856.3 |
| 4 | 4032 | 0 | 0 | 0 | NA | 0 | 50 | 600 | 500 | 1150 | 750 |
| 4 | 4041 | 0 | 0 | 0 | 0 | 400 | 700 | 0 | 50 | 150 | 750 |
| 4 | 4045 | 0 | 0 | 0 | 0 | 0 | 0 | 0 | 0 | 200 | 900 |
| 4 | 4050 | 0 | 0 | 0 | 0 | 0 | 0 | 250 | 700 | 1200 | 2000 |
| 4 | 4051 | 0 | 0 | 0 | 0 | 0 | 300 | 950 | 1400 | 450 | 700 |
| 4 | 4054 | 0 | NA | 0 | 0 | 0 | 350 | 2500 | 700 | 650 | 1300 |
| 4 | 4055 | 0 | 0 | 0 | 50 | 0 | 800 | 850 | 5550 | 3450 | 6700 |
| 4 | 4058 | 0 | 0 | 0 | NA | 0 | 0 | 0 | 0 | 0 | 0 |
| 4 | 4059 | 0 | 0 | 0 | NA | 0 | 0 | 0 | 0 | NA | 0 |

TABLE 3-continued

Fecal egg counts

| Group | Pig ID | 6/21 | 6/28 | 7/6 | 7/12 | 7/19 | 7/26 | 8/2 | 8/9 | 8/16 | Aug. 23, 2010 (necropsy) |
|---|---|---|---|---|---|---|---|---|---|---|---|
| 4 | 4075 | 0 | NA | 0 | 0 | 0 | 0 | 0 | 0 | 0 | 0 |
| 4 | 4082 | 0 | 0 | 0 | 0 | 0 | 100 | 50 | 350 | 250 | 750 |
| 4 | 4087 | 0 | 0 | 0 | 0 | 0 | 0 | 150 | 50 | 500 | 1450 |
| 4 | 4090 | 0 | 0 | 0 | 0 | 0 | 0 | 0 | 0 | 0 | 0 |
| 4 | 4151 | 0 | 0 | 0 | 0 | 0 | 0 | 0 | 0 | 0 | 0 |
| 4 | 4154 | 0 | 0 | 0 | 0 | 0 | 0 | 250 | 600 | 900 | 1400 |
| 4 | 4155 | 0 | 0 | 0 | 0 | 0 | 0 | 50 | 0 | 0 | 0 |
| Mean EPG | | 0.0 | 0.0 | 0.0 | 3.8 | 25.0 | 143.8 | 353.1 | 618.8 | 593.3 | 1043.8 |
| days post 1st infection | | 28 | 35 | 42 | 49 | 56 | 63 | 70 | 77 | 84 | 91 |
| weeks post 1st infection | | 4 | 5 | 6 | 7 | 8 | 9 | 10 | 11 | 12 | 13 |

FIGS. 2 and 3 show that eggs were first detected in one pig at week 7 post-infection, and then the numbers of pigs shedding eggs in their feces and the level of egg shedding (in eggs per gram) continued to increase each week through the remainder of the study. As measured in eggs per gram (EPG), Groups 1 and 4 remained consistently higher than Groups 2 and 3. Mean EPG of Groups 2 and 3 remained relatively low through week 11, when the FEC of Group 3 began to rise. By week 13 the mean FEC of group 3 pigs increased to near the levels seen for groups 1 and 4, however the FEC of group 2 remained low. It is unknown how FEC might have changed in week 14 because all animals were euthanized at week 13, but given the relatively low mean worm counts measured for group 2, it is highly likely that the FEC of group 2 would have remained low had the pigs not been euthanized. The apparent delay in egg shedding seen in groups 2 and 3, both in numbers of pigs shedding eggs and in the magnitude of the EPG, may have been due to an inhibition of worm development induce by the essential oil-comprising experimental blend, or may simply be a reflection of the smaller worm burdens in these groups. Because all worms were mature by the time necropsies were performed it is not possible to differentiate these possibilities. To determine this would require an additional study where pigs are necropsied at two different intervals following infection.

The direct comparisons made between the control group (group 4) and the Group 2 essential oil-comprising experimental blend, revealed a significant difference between the groups for FEC (p-value=0.02).

Table 4 shows the data recorded for worm counts, worm volume, and the final FEC. Table 5 showed the percent reductions in worm counts, worm volume and FEC. FIG. 4 showed this same data in a graph.

The Group 1 essential oil-comprising experimental blend appeared to have little effect on the worm burdens of the pigs. However, based on the observed reduction in worm counts, there appeared to be a dose dependent effect of the Groups 2 and 3 essential oil-comprising experimental blends on the number of parasites infecting the pigs. The Groups 2 and 3 essential oil-comprising experimental blends at doses of 1.0 and 0.5 mg/kg yielded a reduction in worm counts of 76.8% and 39.3%, respectively. The level of reduction in worms for the Group 2 (1.0 mg/kg) dose was statistically significant (p-value=0.0033).

There also was a significant reduction in numbers of female worms for the Group 2 (1.0 mg/kg) dose (p-value=0.0006) compared to the control group (group 4). The direct comparisons made between the control group (group 4) and the Group 2 (1.0 mg/kg) dose, revealed significant differences for both numbers of male worms (p-value=0.0073) and worm volume (p-value=0.0160).

TABLE 4

Worm counts and worm volume.

| Group 1 (1.0 mg/kg) | | | | Group 2 (1.0 mg/kg) | | | |
|---|---|---|---|---|---|---|---|
| Animal ID | Worm count | Displaced volume (ml) | Final Egg Count | Animal ID | Worm count | Displaced volume (ml) | Final Egg Count |
| 4031 | 54 | 58 | 2150 | 4035 | 2 | 4 | 0 |
| 4037 | 1 | 3 | 350 | 4043 | 0 | 0 | 100 |
| 4042 | 0 | 0 | 0 | 4048 | 5 | 16 | 0 |
| 4047 | 35 | 53 | 4300 | 4049 | 2 | 4 | 0 |
| 4053 | 15 | 33 | 800 | 4061 | 1 | 3 | 0 |
| 4060 | 6 | 7 | 250 | 4078 | 6 | 11 | 1050 |
| 4062 | 38 | 54 | 2000 | 4080 | 7 | 11 | 400 |
| 4077 | 7 | 14 | 950 | 4083 | 4 | 8 | 200 |
| 4086 | 1 | 2 | 0 | 4085 | 16 | 40 | 1600 |
| 4092 | 2 | 6 | 50 | 4091 | 2 | 5 | 150 |
| 4094 | 24 | 41 | 1800 | 4093 | 11 | 12 | 350 |

TABLE 4-continued

Worm counts and worm volume.

| 4100 | 22 | 39 | 950 | 4097 | 1 | 1 | 50 |
|---|---|---|---|---|---|---|---|
| 4145 | 0 | 0 | 0 | 4099 | 6 | 28 | 1350 |
| 4146 | 8 | 13 | 650 | 4143 | 0 | 0 | 0 |
| 4150 | 13 | 12 | 0 | 4148 | 0 | 0 | 0 |
|  |  |  |  | 4152 | 0 | 0 | 0 |
| Percent Positive | 86.7 |  | 80.0 | Percent Positive | 75.0 |  | 56.3 |
| MEAN | 15.1 | 22.3 | 950.0 | MEAN | 3.9 | 8.9 | 328.1 |
| Std Dev | 16.5 | 21.6 | 1191.3 | Std Dev | 4.5 | 11.2 | 524.1 |

| Group 3 (0.5 mg/kg) | | | | Group 4 Placebo | | | |
|---|---|---|---|---|---|---|---|
| Animal ID | Worm count | Displaced volume (ml) | Final Egg Count | Animal ID | Worm count | Displaced volume (ml) | Final Egg Count |
| 4026 | 1 | 4 | 0 | 4032 | 15 | 25 | 750 |
| 4027 | 14 | 22 | 950 | 4041 | 17 | 23 | 750 |
| 4028 | 0 | 0 | 0 | 4045 | 46 | 46 | 900 |
| 4030 | 1 | 2 | 0 | 4050 | 22 | 38 | 2000 |
| 4034 | 38 | 70 | 4550 | 4051 | 59 | 53 | 700 |
| 4038 | 10 | 21 | 1150 | 4054 | 5 | 16 | 1300 |
| 4044 | 3 | 4 | 200 | 4055 | 48 | 90 | 6700 |
| 4046 | 32 | 30 | 2000 | 4058 | 1 | 1 | 0 |
| 4056 | 0 | 0 | 0 | 4059 | 3 | 11 | 0 |
| 4076 | 0 | 0 | 50 | 4075 | 0 | 0 | 0 |
| 4084 | 0 | 0 | 0 | 4082 | 3 | 10 | 750 |
| 4088 | 0 | 0 | 0 | 4087 | 12 | 16 | 1450 |
| 4095 | 37 | 28 | 950 | 4090 | 1 | 1 | 0 |
| 4096 | 12 | 12 | 400 | 4151 | 0 | 0 | 0 |
| 4144 | 7 | 10 | 950 | 4154 | 40 | 55 | 1400 |
| 4149 | 10 | 22 | 2500 | 4155 | 0 | 0 | 0 |
| Percent Positive | 68.8 |  | 62.5 | Percent Positive | 81.3 |  | 62.5 |
| MEAN | 10.3 | 14.1 | 856.3 | MEAN | 17.0 | 24.1 | 1043.8 |
| Std Dev | 13.5 | 18.5 | 1250.4 | Std Dev | 20.1 | 26.0 | 1637.1 |

TABLE 5

Percent reductions in worm count, egg count and worm volume as compared to placebo treated control group.

| Tx Group | % Red Worm Count | % Red Egg Count | % Red Worm Volume |
|---|---|---|---|
| 1 | 11.4 | 9.0 | 7.2 |
| 3 | 39.3 | 18.0 | 41.6 |
| 2 | 76.8 | 68.6 | 62.9 |

The hypothesis that essential oil-comprising experimental blends would affect the egg production of female worms was tested by measuring of the ratio of the weight of the uterus as compared to the total worm weight. Statistical analysis of the data yielded no significant effects, thus indicating that ratio of worm weight to uterus weight does not change with the treatment.

Figure 5:
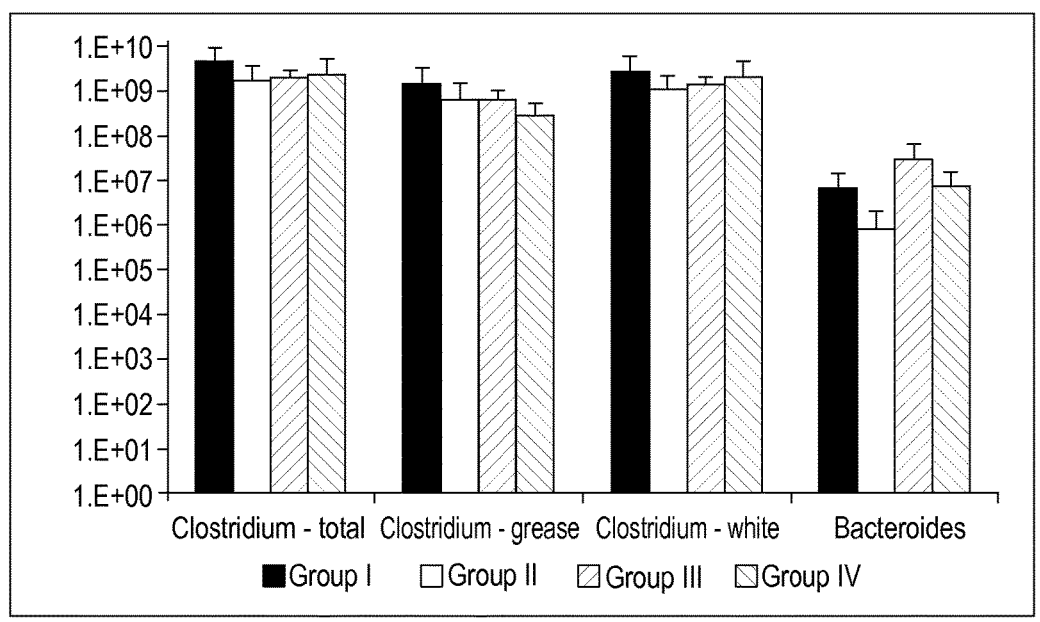
FIG. 5 is a bar graph representing the colon forming units (CFU)/gm feces for *Clostridium* and *Bacteroides* for four groups of animals infected with *Ascaris suum* and treated with compounds disclosed herein.

No significant differences were detected in lecithinase producing *Clostridium* among the treatments. Significant differences were detected in the count of total *Clostridium* among the treatments. Animals from Group I showed slightly higher counts than animals from Group II. Significant differences were detected in lipase producing *Clostridium* among the treatments. Animals from Group I showed higher counts of lipase producing *Clostridium* than animals from Group IV (placebo). Significant differences were detected in *Bacteroides* counts among the treatments. Animals from Group II presented fewer *Bacteroides* than animals from Group I, Group III and Group IV (FIG. 5).

TABLE 6

CFU/gm feces for the four groups of pigs

| Treatment | Costridium - total (CFU/ g of feces) | Clostridium - greasy CFU/ g of feces) | Clostridium - white (CFU/ g of feces) | Bacteroides (CFU/g of feces) |
|---|---|---|---|---|
| Group I | $4.1 \times 10^9$ A | $1.4 \times 10^9$ A | $2.6 \times 10^9$ A | $6.7 \times 10^6$ A* |
| Group II | $1.6 \times 10^9$ B | $6.4 \times 10^8$ AB | $1.0 \times 10^9$ A | $8.4 \times 10^5$ B |
| Group III | $1.9 \times 10^9$ AB | $6.5 \times 10^8$ AB | $1.3 \times 10^9$ A | $3.0 \times 10^7$ A |
| Group IV (placebo) | $2.1 \times 10^9$ AB | $2.7 \times 10^8$ B | $1.9 \times 10^9$ A | $7.3 \times 10^6$ A |
| P value | 0.04 | 0.02 | 18.21 | 0.001 |
| CV % | 436 | 530 | 521 | 960 |

*Different letters in the same column indicate statistical difference (P < 0.05) evaluated by Tukey test.

While there is copious research investigating the role of the intestinal microbiota in intestinal health, there are very few hard facts that can be used to predict health status. An abundant *Bacteroides* status is desired for the large intestine because *Bacteroides* have been shown to promote the development of intestinal mucosa, mesenteric nerves, and the secretory immune system (Peyer's patches). However the levels (dose) of *Bacteroides* needed to produce these effects in young animals is not known and a slight decrease in *Bacteroides* levels has not been consistently shown to indicate a change in intestinal health. In the study described above, Group II possessed statistically fewer *Bacteroides* than the other groups. However it is not clear whether the differences, which were less than 1 log, are biologically relevant or indicate a decrease in intestinal health status.

The Clostridia are generally viewed as undesirable members of the large intestinal microbial consortium although they are consistently among the most abundant groups detected. In the study described above, abundant *Clostridium* were detected among all of the experimental groups although Group 4 possessed significantly fewer total *Clostridium*. Without evidence of pathological changes in the intestine, it is not known whether the differences are biologically relevant or indicate a change in intestinal health status. Pathogenic *Clostridium* possess hydrolytic enzymes such as glycosylhydrolases, lipases, and proteases that can potentially damage the intestine. For example, the principal virulence factor of *Clostridium perfringens*, the causative agent of gas gangrene and necrotic enteritis, is a phospholipase C (lecithinase-alpha-toxin). Lecithinase has high activity on intestinal cell membranes and can produce necrosis of the intestinal mucosa. Many *Clostridium* produce other types of lipase activity whose contribution to intestinal disease is considered minor and the signals that trigger pathogenic behavior of *Clostridium* are still poorly understood. In the study described above, high levels of lecithinase and lipase producing *Clostridium* were detected in all of the experimental groups. While the levels of *Clostridium* that have the ability to produce lecithinase was high in all groups, without pathological evidence of intestinal damage, it is unlikely that the bacteria were actually producing lecithinase within the intestine. Although Group 4 had statistically fewer lipase producers than the other groups, without additional evidence of a change in intestinal health status, it is not known whether this difference is biologically relevant This study was conducted to investigate the effectiveness of three anthelmintic-like essential oil-comprising blends as a "functional food" source against *Ascaris suum* in a pig model. The protocol used was designed taking into account the biology of *A. suum* and the need for extended contact time with the test article. Four groups of 16 female pigs were included in the study; one group served as an untreated control which received daily treatment with control article at a dosage equivalent of 1.0 mg/kg (group 4) and the other 3 groups received essential oil-comprising blends. Treatments were started after an initial 3-day acclimation period, and were continued daily (7 days per week) throughout the study until the day of necropsy. After daily treatment for 3 days, pigs were inoculated with *Ascaris suum* eggs at a dose of 20 eggs/kg/week for 4 weeks (total inoculum=approximately 963 eggs per pig). Pigs were weighed weekly throughout the study and fecal egg counts were performed weekly starting on week 6. Thirteen weeks after the final inoculation with *A. suum* eggs pigs were necropsied and worms were recovered, counted and measured.

The Group 1 essential oil-comprising blend appeared to have little effect on the worm burdens of the pigs. However, based on the observed reduction in worm counts, there appeared to be a dose dependent effect of the Group 2 and Group 3 essential oil-comprising blends on the number of parasites infecting the pigs. The Group 2 and Group 3 essential oil-comprising blends at doses of 1.0 and 0.5 mg/kg yielded a reduction in worm counts of 76.8% and 39.3%, respectively. However, the reduction in worms was statistically significant (p-value=0.0033) only for the Group 2 (1.0 mg/kg) dose.

There also was a significant reduction in numbers of female worms for the Group 2 (1.0 mg/kg) essential oil-comprising blend (p-value=0.0006) compared to the control group. The direct comparisons made between the control group (group 4) and the Group 2 (1.0 mg/kg) essential oil-comprising blend, revealed significant differences for both numbers of male worms (p-value=0.0073) and worm volume (p-value=0.0160). Female worms were much larger than male worms, produce huge numbers of eggs that are stored in the uterus (a single female worm can have several million eggs in her uterus), and must consume far greater nutritive resources than male worms to produce those eggs. Consequently, female worms have a much greater impact on the health of the host and on the contamination of the environment with infective eggs, which ultimately is responsible for the continuation of the infection cycle in the host population. Thus, a reduction in female worms is more important than a reduction in male worms. The data clearly show that the Group 2 (1.0 mg/kg) essential oil-comprising blend significantly reduced total numbers of worms, but importantly, also seems to have a greater effect on the female worms.

As measured in eggs per gram (EPG), groups 1 and 4 remained consistently higher than groups 2 and 3. Mean EPG of groups 2 and 3 remained relatively low through week 11, when the FEC of group 3 began to rise. By week 13 the mean FEC of group 3 pigs increased to near the levels seen for groups 1 and 4, however the FEC of group 2 remains low. It is unknown how FEC might have changed in week 14 because all animals are euthanized at week 13, but given the relatively low mean worm counts measured for group 2, it is highly likely that the FEC of group 2 would have remained low had the pigs not been euthanized. The apparent delay in egg shedding seen in groups 2 and 3, both in numbers of pigs shedding eggs and in the magnitude of the EPG, may have been due to an inhibition of worm development induced by one of the essential oil-comprising blends, or may simply be a reflection of the smaller worm burdens in these groups. Because all worms are mature by the time necropsies were performed it is not possible to differentiate these possibilities. To determine this would require an additional study where pigs are necropsied at two different intervals following infection.

The direct comparisons made between the control group (group 4) and the Group 2 (1.0 mg/kg) blend, revealed a significant difference between the groups for FEC (p-value=0.02). Analysis of weight data revealed significant differences across time for all treatment groups.

The administration of each of the three essential oil-comprising blends was well tolerated by all pigs and did not cause any apparent or clinically measurable adverse effects on the health of the young growing pigs. The Group 2 blend administered at a dose of 1.0 mg/kg yielded a statistically and a biologically significant reduction in total worm counts and numbers of female worms compared to untreated controls. Other parameters such as numbers of male worms, worm volume, and fecal egg counts approached significance, but p-values were greater than 0.05 and so were not considered statistically significant. Lack of significance was likely due to the high level of variability in the data among the four groups. Comparing only the group of pigs receiving the Group 2 blend administered at a dose of 1.0 mg/kg to the placebo control group yielded statistically significant results for all parameters. Groups of pigs receiving either the Group 1 blend, or the Group 3 blend demonstrated no statistically significant differences among the parameters tested compared to the control group.

The pig *Ascaris suum* model was selected because this model most closely resembles human infection with *Ascaris lumbricoides*, the most prevalent parasitic infection worldwide. The biology, host-parasite interactions, and population dynamics of these two parasites are extremely similar. Consequently, this model is the most ideal for this study. However, this model also poses some important biological challenges in research studies. In most studies, only about 66-75% of pigs develop patent infections following experimental inoculations, and the resulting parasite burdens in the pigs are highly overdispersed. This means that some pigs will have no worms, many pigs will have small to moderate numbers of worms, and a few pigs will have large numbers of worms. Consequently, there is always an inherent very high level of variability in the data, which will reduce the power to detect differences among treatment groups. Due to the high level of variability in the data that is to be expected, large group sizes are needed to have sufficient power to demonstrate statistical significance of treatment effects.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

What is claimed is:

1. A formulation for treating a parasitic infection in a subject comprising:
    a composition comprising:
        40-75% thymol octanoate, by weight of the composition;
        alpha-pinene;
        linalyl acetate; and
        para-cymene;
    an artificial additive; and
    a carrier.

2. The formulation of claim 1, wherein the composition comprises, by weight of the composition, 20-30% alpha-pinene, 20-30% linalyl acetate, and 20-30% para-cymene.

3. The formulation of claim 1, wherein the parasitic infection is by a protozoan parasite.

4. The formulation of claim 3, wherein the protozoan parasite is selected from the group consisting of an intestinal protozoan, a tissue protozoan, and a blood protozoan.

5. The formulation of claim 3, wherein the protozoan parasite is at least one of *Entamoeba hystolytica, Giardia lamblia, Cryptosporidium muris, Cryptosporidium parvum, Trypanosomatida gambiense, Trypanosomatida rhodesiense, Trypanosomatida crusi, Leishmania mexicana, Leishmania braziliensis, Leishmania tropica, Leishmania donovani Toxoplasma gondii, Plasmodium vivax, Plasmodium ovate, Plasmodium malariae, Plasmodium falciparum, Trichomonas vaginalis*, and *Histomonas meleagridis*.

6. The formulation of claim 1, wherein the parasitic infection is by a helminthic parasite.

7. The formulation of claim 6, wherein the helminthic parasite is a nematode.

8. The formulation of claim 7, wherein the helminthic parasite is a member of class Adenophorea.

9. The formulation of claim 7, wherein the helminthic parasite is a member of class Secernentea.

10. The formulation of claim 7, wherein the helminthic parasite is at least one of *Trichuris trichiura, Ascaris lumbricoides, Enterobius vermicularis, Ancylostoma duodenale, Necator americanus, Strongyloides stercoralis, Wuchereria bancrofti*, and *Dracunculus medinensis*.

11. The formulation of claim 6, wherein the helminthic parasite is a trematode.

12. The formulation of claim 11, wherein the helminthic parasite is selected from the group consisting of a blood fluke, a liver fluke, an intestinal fluke, and a lung fluke.

13. The formulation of claim 11, wherein the helminthic parasite is at least one of *Schistosoma mansoni, Schistosoma haematobium, Schistosoma japonicum, Fasciola hepatica, Fasciola gigantica, Heterophyes heterophyes, Paragonimus westermani*, and *Opishorchis sinensis*.

14. The formulation of claim 6, wherein the helminthic parasite is a cestode.

15. The formulation of claim 14, wherein the helminthic parasite is least one of *Taenia solium, Taenia saginata, Hymenolepis nana, Echinococcus granulosus*, and *Diplyidium caninum*.

16. The formulation of claim 1, wherein the carrier comprises a prepared food product.

17. The formulation of claim 16, wherein the prepared food product comprises the artificial additive.

18. The formulation of claim 17, wherein the artificial additive is included to produce an effect in the formulation.

19. The formulation of claim 18, wherein the effect is selected from the group consisting of modification of flavor, modification of color, increase in shelf life, and enhancement of nutritional value.

20. The formulation of claim 16, wherein the prepared food product is one of a beverage and a drink mix.

21. The formulation of claim 16, wherein the prepared food product comprises a cereal.

22. The formulation of claim 1, wherein the artificial additive comprises at least one of a suspending agent and a preservative.

23. The formulation of claim 22, wherein the artificial additive is a suspending agent comprising hydrogenated edible fats.

24. The formulation of claim 22, wherein the artificial additive is a preservative selected from the group consisting of methyl hydroxybenzoate and propyl-p-hydroxy-benzoate.

25. The formulation of claim 1, wherein the artificial additive comprises an excipient.

26. The formulation of claim 1, wherein the artificial additive comprises at least one of a stabilizing agent and a dispersing agent.

27. The formulation of claim 25, wherein the excipient is selected from the group consisting of a binding agent, a filler, a disintegrant, and a wetting agent.

28. The formulation of claim 27, wherein the excipient is a binding agent selected from the group consisting of pre-gelatinized maize starch, polyvinylpyrrolidone, and hydroxypropyl methylcellulose.

29. The formulation of claim 27, wherein the excipient is a filler selected from the group consisting of microcrystalline cellulose and calcium hydrogen phosphate.

30. The formulation of claim 27, wherein the excipient is a disintegrant comprising sodium starch glycollate.

31. The formulation of claim 27, wherein the excipient is a wetting agent comprising sodium lauryl sulphate.

32. A formulation for treating a parasitic infection in a subject comprising:
 a composition consisting of:
  40-75% thymol octanoate, by weight of the composition;
  alpha-pinene;
  linalyl acetate; and
  para-cymene;
 an artificial additive; and
 a carrier.

33. The formulation of claim 32, wherein the carrier comprises a prepared food product.

34. The formulation of claim 33, wherein the prepared food product comprises one of a beverage and a drink mix.

35. The formulation of claim 33, wherein the prepared food product comprises a cereal.

36. The formulation of claim 33, wherein the prepared food product comprises the artificial additive.

37. The formulation of claim 36, wherein the artificial additive is included to produce an effect in the formulation.

38. The formulation of claim 37, wherein the effect is selected from the group consisting of modification of flavor, modification of color, increase in shelf life, and enhancement of nutritional value.

39. The formulation of claim 32, wherein the artificial additive comprises at least one of a suspending agent and a preservative.

40. The formulation of claim 39, wherein the artificial additive comprises a suspending agent comprising hydrogenated edible fats.

41. The formulation of claim 39, wherein the artificial additive comprises a preservative selected from the group consisting of methyl hydroxybenzoate and propyl-p-hydroxy-benzoate.

42. The formulation of claim 32, wherein the artificial additive comprises an excipient.

43. The formulation of claim 32, wherein the artificial additive comprises at least one of a stabilizing agent and a dispersing agent.

44. The formulation of claim 42, wherein the excipient is selected from the group consisting of a binding agent, a filler, a disintegrant, and a wetting agent.

45. The formulation of claim 44, wherein the excipient is a binding agent selected from the group consisting of pre-gelatinized maize starch, polyvinylpyrrolidone, and hydroxypropyl methylcellulose.

46. The formulation of claim 44, wherein the excipient is a filler selected from the group consisting of microcrystalline cellulose and calcium hydrogen phosphate.

47. The formulation of claim 44, wherein the excipient is a disintegrant comprising sodium starch glycollate.

48. The formulation of claim 44, wherein the excipient is a wetting agent comprising sodium lauryl sulphate.

* * * * *